US008747318B2

(12) United States Patent
Shiina et al.

(10) Patent No.: US 8,747,318 B2
(45) Date of Patent: Jun. 10, 2014

(54) ULTRASONIC MEASUREMENT APPARATUS

(75) Inventors: Tsuyoshi Shiina, Kyoto (JP); Yasuhiro Someda, Yokohama (JP); Kenichi Nagae, Yokohama (JP); Katsuya Oikawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 270 days.

(21) Appl. No.: 12/433,006

(22) Filed: Apr. 30, 2009

(65) Prior Publication Data

US 2009/0275837 A1 Nov. 5, 2009

(30) Foreign Application Priority Data

May 2, 2008 (JP) ................................ 2008-120326

(51) Int. Cl.
*A61B 8/00* (2006.01)
(52) U.S. Cl.
USPC .......................................... 600/438; 73/627
(58) Field of Classification Search
USPC ......... 600/437, 438, 439, 448, 449, 450, 451, 600/452, 459, 587; 73/584, 597
See application file for complete search history.

(56) References Cited

U.S. PATENT DOCUMENTS

| 4,434,661 | A | * | 3/1984 | Miwa et al. ................ 73/625 |
| 4,646,754 | A | * | 3/1987 | Seale ....................... 600/587 |
| 4,771,792 | A | * | 9/1988 | Seale ....................... 600/587 |
| 5,178,147 | A | | 1/1993 | Ophir et al. ............ 128/600.01 |
| 5,474,070 | A | * | 12/1995 | Ophir et al. ................. 600/437 |
| 6,685,644 | B2 | | 2/2004 | Seo et al. .................. 600/447 |
| 2008/0306371 | A1 | | 12/2008 | Fukutani et al. ............ 600/407 |

FOREIGN PATENT DOCUMENTS

| EP | 32513 | 7/1980 |
| JP | S55-103839 | 8/1980 |
| JP | 05-161647 | 6/1993 |
| JP | 09-313486 | 12/1997 |
| JP | 2001-276070 | 10/2001 |
| JP | 2003-10186 | 1/2003 |
| JP | 2005-137581 | 6/2005 |
| JP | 2005-152192 | 6/2005 |
| JP | 2005-160704 | 6/2005 |

(Continued)

OTHER PUBLICATIONS

Udomchai Techavipoo et al., "Estimation of Displacement Vectors and Strain Tensors in Elastography Using Angular Insonifications", *2004 IEEE Int'l. Ultrasonics, Ferroelectrics & Frequency Control Joint 50th Anniversary Conference, 2004 IEEE Ultrasonics Symposium*, pp. 40-43 (2004).

(Continued)

*Primary Examiner* — Unsu Jung
*Assistant Examiner* — Phong K Huynh
(74) *Attorney, Agent, or Firm* — Fitzpatrick, Cella, Harper & Scinto

(57) ABSTRACT

A sample moves, either naturally (as in the case of the heart) or by application of force, and its movement is measured. A processing unit calculates first displacement related information concerning a first direction of the object to be measured (the sample) by using data in either one of an increase period and a decrease period of the force applied to the objected to be measured, from data received by a first ultrasonic probe. In addition, the processing unit calculates second displacement related information concerning a second direction of the object to be measured by using data in the same period as that used to calculate the first displacement related information, from data received by a second ultrasonic probe.

13 Claims, 11 Drawing Sheets

(56) References Cited

FOREIGN PATENT DOCUMENTS

| | | |
|---|---|---|
| JP | 2006-325704 | 12/2006 |
| JP | 2006-340745 | 12/2006 |
| JP | 2007-307042 | 11/2007 |
| WO | WO 01/85031 | 11/2001 |
| WO | WO 2005/120358 | 12/2005 |
| WO | WO 2007/047046 A1 | 4/2007 .............. G01S 15/89 |

OTHER PUBLICATIONS

JPO Office Action issued Feb. 19, 2013 in counterpart Japanese Patent Application No. 2008-120326, with partial translation.

* cited by examiner

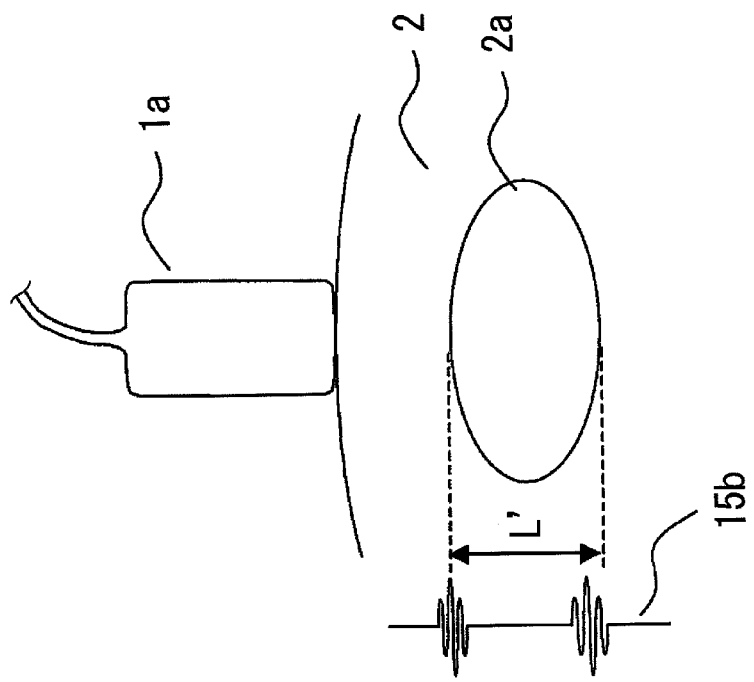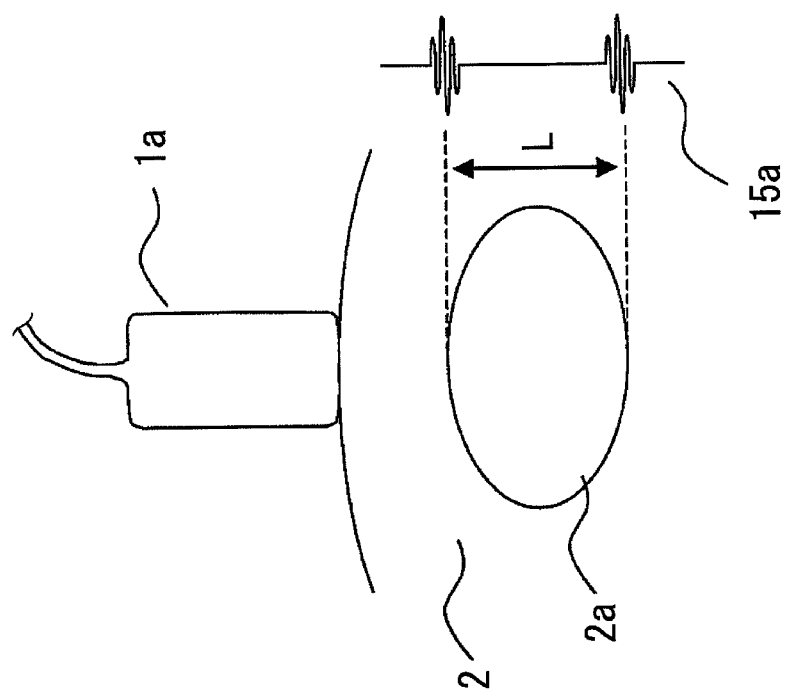

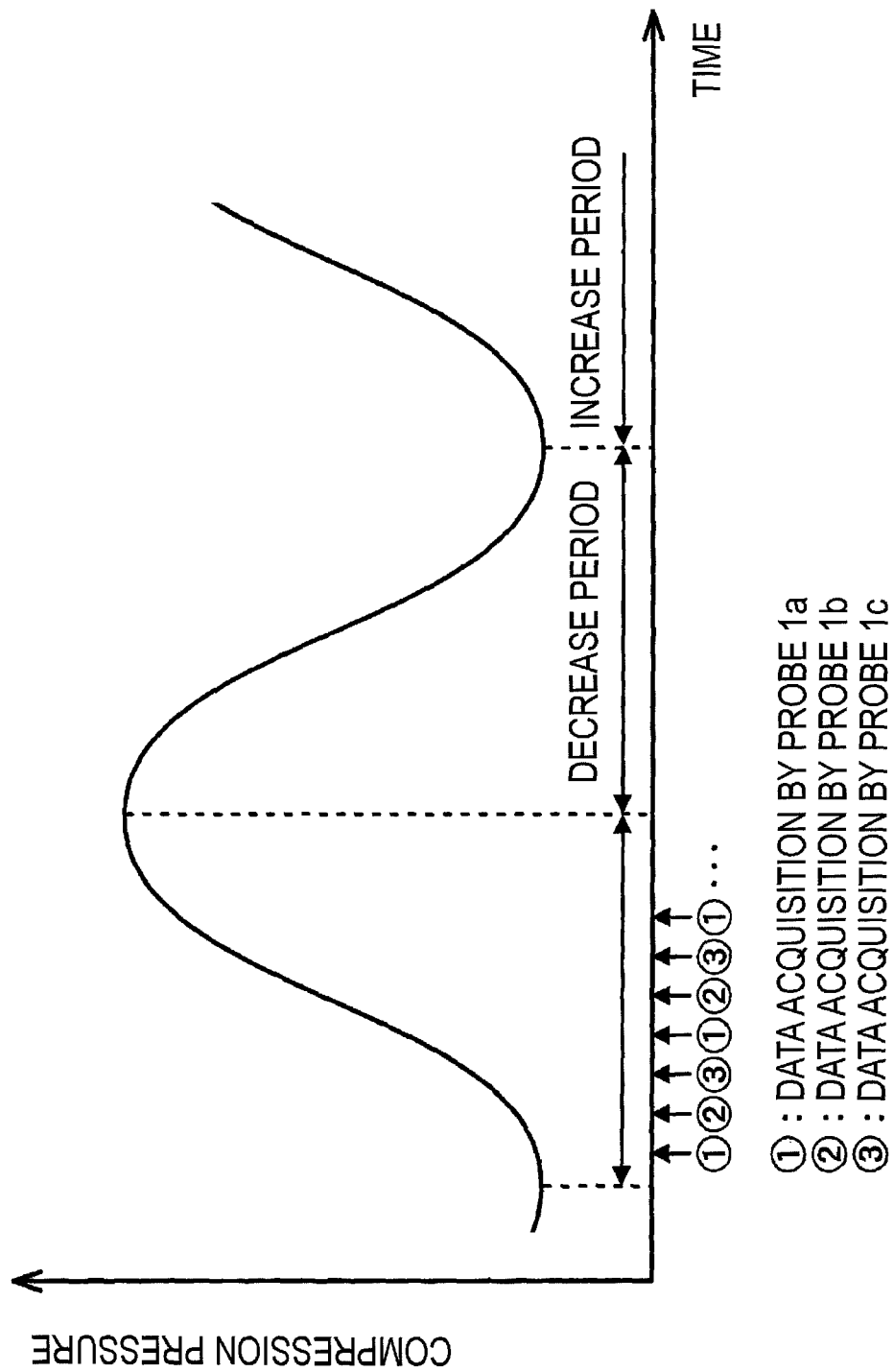

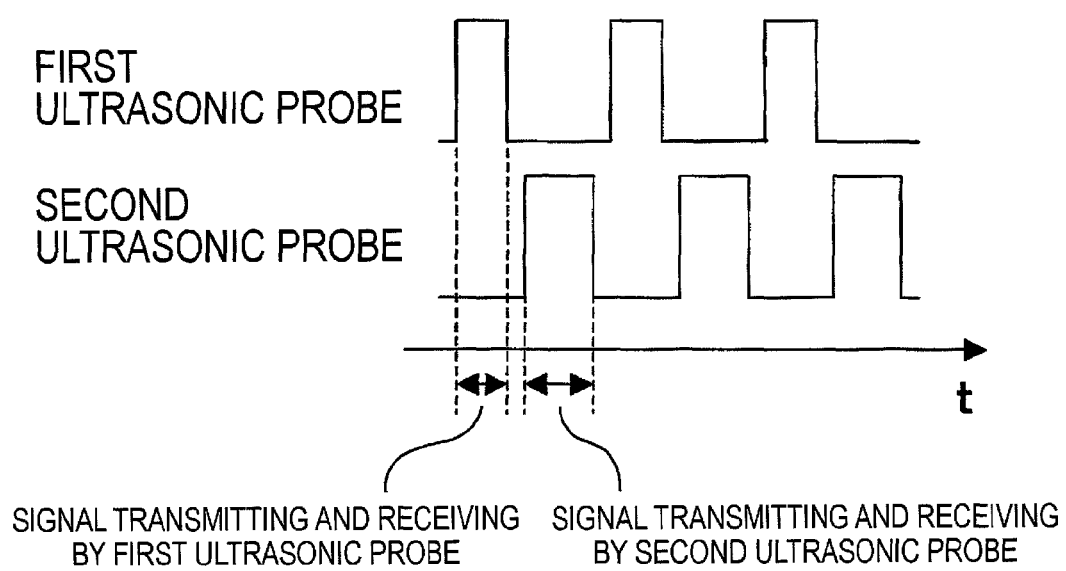

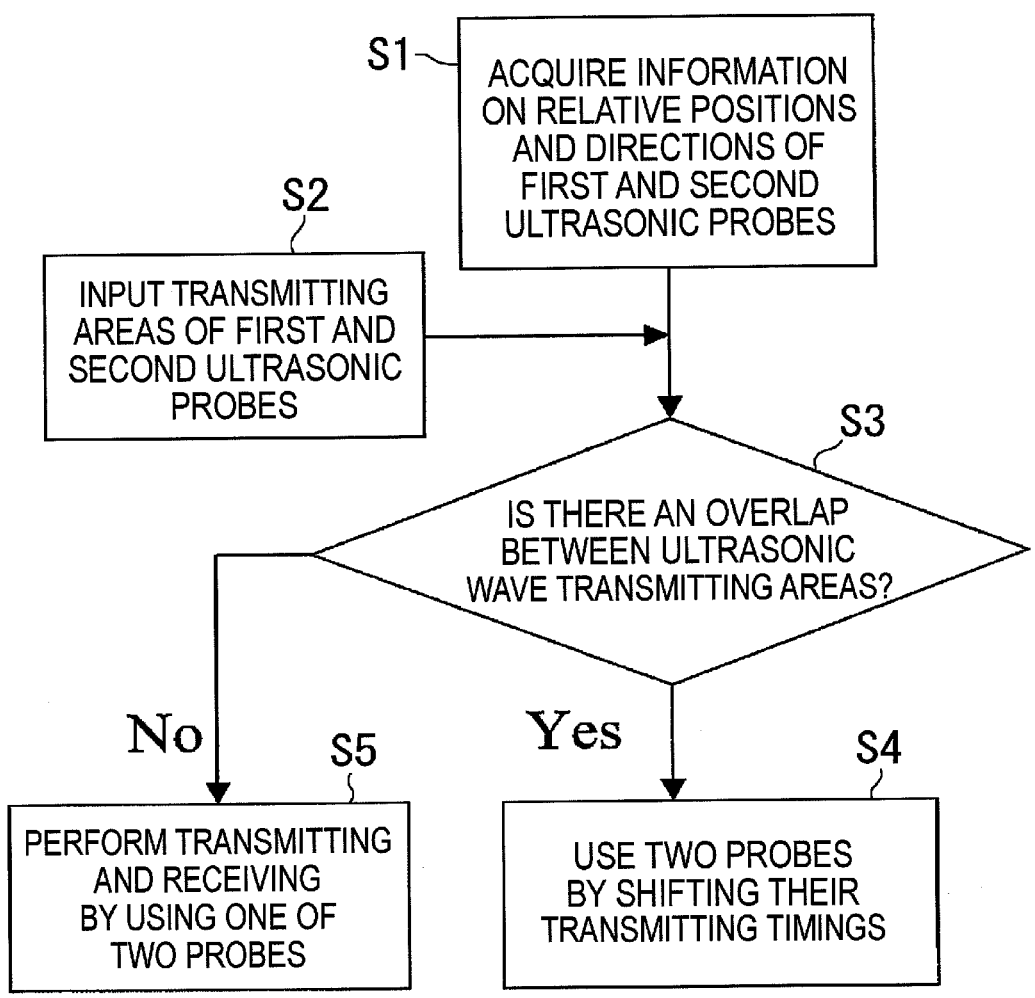

ULTRASONIC MEASUREMENT APPARATUS

RELATED APPLICATIONS

This application claims the benefit of Japanese Patent Application No. 2008-120326, filed on May 2, 2008, which is hereby incorporated by reference herein in its entirety.

BACKGROUND OF THE INVENTION

1. Field of the Invention

The present invention relates to an ultrasonic measurement apparatus that acquires tomographic images or three-dimensional images of an object to be measured by using ultrasonic waves, and more particularly, it relates to an ultrasonic measurement apparatus that acquires a strain characteristic and an elastic property of a sample.

2. Description of the Related Art

An apparatus for acquiring tomographic images by using conventional general ultrasonic waves is constructed to include, as its components, a transmitting unit for transmitting an ultrasonic wave to an object to be measured (sample), a receiving unit for receiving a reflection wave, a scanning unit for scanning the transmitted and received waves, and a unit for converting and visualizing the received reflection signal into a corresponding luminance signal. The interior of the sample is observed by using time series tomographic images acquired by these components. In addition, in one form of the apparatus, three-dimensional images are obtained by scanning an ultrasonic wave in the up and down directions as well as in the right and left directions by means of the above-mentioned scanning unit.

In recent years, there have also been studied a method of generating a strain in the interior of a sample in an artificial manner by compressing a surface of the sample, and measuring the strain by processing ultrasonic signals, or a method of imaging an elastic modulus such as Young's modulus, etc.

In the specification of U.S. Pat. No. 5,178,147, it is described that the elastic property of a sample is measured by compressing the sample in a vertical direction and measuring a relative positional change of each point or location. In addition, in a case where the sample, being an elastic member, has motion of its own, it is possible to measure a strain only by means of the processing of ultrasonic signals without performing such a compressing operation as described above.

In addition, Japanese Patent Application Laid-Open No. H 9-313486 discloses a method of measuring a variation in the thickness of a cardiac muscle based on a relative positional variation between two points of a cardiac wall.

SUMMARY OF THE INVENTION

What is common to the techniques disclosed in the specification of U.S. Pat. No. 5,178,147 and Japanese Patent Application Laid-Open No. H 9-313486 is to measure an amount of positional shift (displacement) of each point inside a sample by computing or processing an ultrasonic signal obtained by a single ultrasonic probe. In addition, according to the above-mentioned documents, the compression of the sample and the measurement of the ultrasonic signal are performed only in one direction.

Although in a case where a displacement or strain of the sample is generated only in the compression direction (e.g., in the propagation direction of the transmitted and received ultrasonic waves), it is possible to obtain information with a high degree of accuracy with measurements by the use of a single ultrasonic probe as stated above, but in actuality, the sample is often displaced or strained in other directions besides the direction of compression.

Accordingly, in a case where a sample which is also strained in directions different from the direction of compression is measured by using the above-mentioned related conventional art or the like, sufficient information has not been obtained on the displacement and/or strain of the sample.

Accordingly, the present invention provides an ultrasonic measurement apparatus which is capable of outputting not only information on a displacement and/or strain of an object to be measured in one direction but also information on displacements and/or strains thereof in a plurality of directions.

The present invention adopts the following construction.

An ultrasonic measurement apparatus of the present invention includes:

a plurality of ultrasonic probes that include, at least, a first ultrasonic probe and a second ultrasonic probe;

an information acquisition unit that acquires information on whether an increase period or an decrease period, the increase period being a period in which a temporal change of a force applied to an object to be measured or an amount of deformation of the object to be measured indicates a tendency of increase, the decrease period being a period in which the temporal change of the force or the amount of deformation indicates a tendency of decrease;

a transmitting circuit that inputs signals for transmitting ultrasonic waves to the first and second ultrasonic probes;

a receiving circuit that receives signals produced by the first and second ultrasonic probes upon reception of ultrasonic waves;

a processing unit;

an output unit; and a system control unit that controls the transmitting circuit, the receiving circuit, the processing unit, and the output unit;

wherein the first ultrasonic probe receives an ultrasonic wave reflected by the object to be measured which is located in an overlapped portion between an ultrasonic wave transmitting area of the first ultrasonic probe and an ultrasonic wave transmitting area of the second ultrasonic probe, and produces first received data, and the second ultrasonic probe receives an ultrasonic wave reflected by the object to be measured which is located in the overlapped portion, and produces second received data;

the processing unit calculates first displacement related information concerning a first direction of the object to be measured by using data in either one of the increase period and the decrease period among the first received data, and calculates second displacement related information concerning a second direction of the object to be measured by using data in the same period as that used to calculate the first displacement related information among the second received data; and the output unit outputs information on the object to be measured by using the first and second displacement related information.

According to the present invention, an ultrasonic measurement apparatus is provided which can output information concerning displacements or strains in a plurality of directions.

In particular, the present invention can obtain information that reflects an elastic property of an object to be measured more accurately so as to calculate both first displacement related information and second displacement related information from data in an increase period (or data in a decrease period).

Further features of the present invention will become apparent from the following description of exemplary embodiments with reference to the attached drawings.

BRIEF DESCRIPTION OF THE DRAWINGS

FIG. 5 is a view depicting a compressing operation of a probe and acquired signals.

FIG. 9 is a view for explaining a compressing operation and acquisition timings of ultrasonic wave data in the first example.

FIG. 10 is a view for explaining the transmitting and receiving timings of a plurality of probes.

FIG. 11 is a flow chart for controlling switching between the transmitting timings of the probes.

DESCRIPTION OF THE PREFERRED EMBODIMENTS

First of all, before describing embodiments of the present invention, certain words or terms used herein are defined as follows.

"Displacement related information" is a displacement (a change in position) itself of an object to be measured, or information that is calculated from such a displacement, and "information calculated from a displacement" includes, for example, a strain, elastic modulus (elastic coefficients), hardness (softness), etc., of the object to be measured. These pieces of displacement related information can be treated as variables that depend on the hardness (difficulty of deformation) of the object to be measured).

Now, reference will be made to an ultrasonic measurement apparatus according to a preferred embodiment of the present invention with reference to the accompanying drawings.

Although in this embodiment, a medical ultrasonic diagnostic apparatus is shown as one example of the ultrasonic measurement apparatus, it is needless to say that the present invention is not limited to medical ultrasonic diagnostic apparatuses, but can be applied to other apparatuses such as flaw detectors used for measurements of elastic materials, etc.

Figure 1:
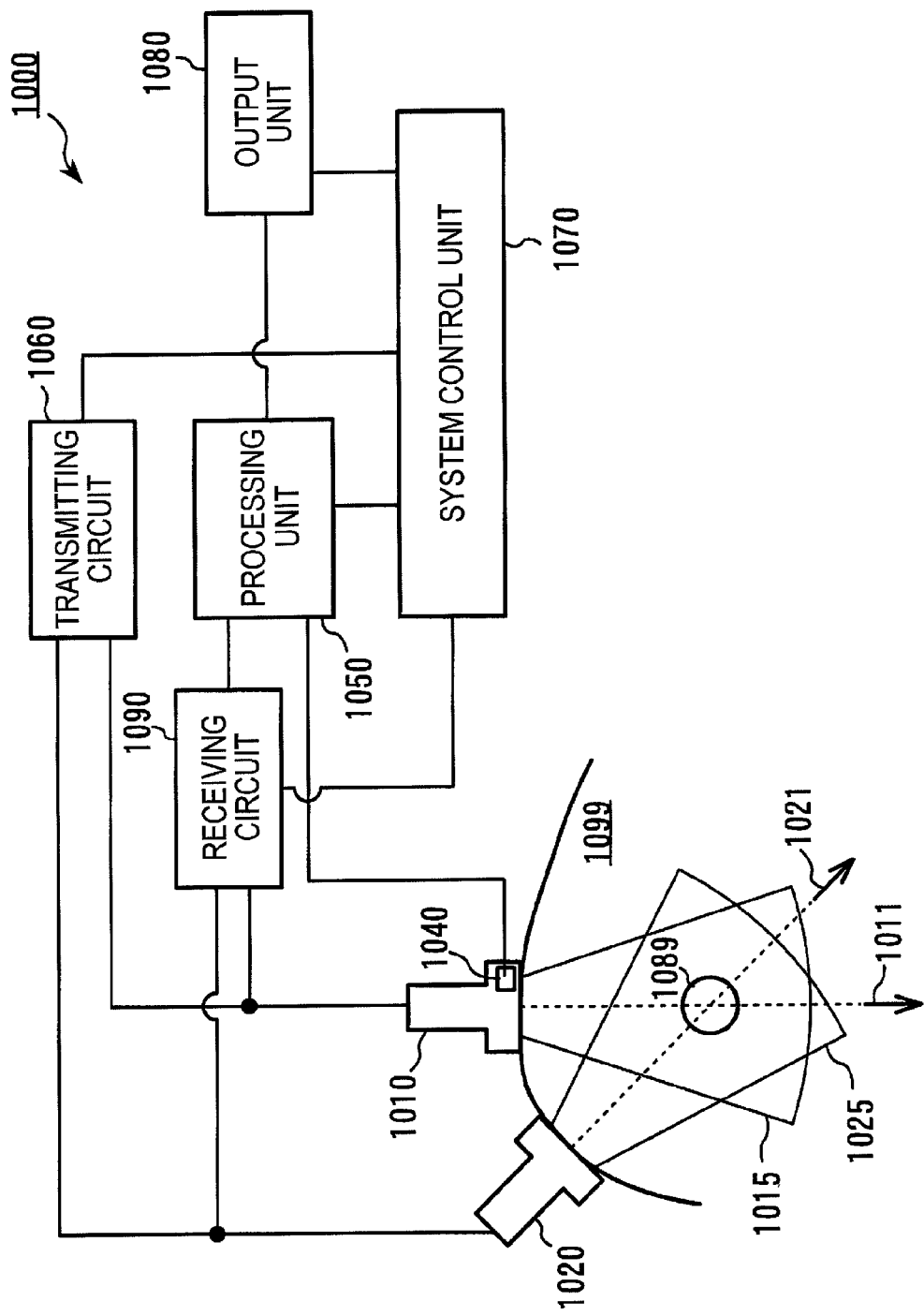
FIG. 1 depicts the construction of an ultrasonic measurement apparatus according to one embodiment of the present invention.

FIG. 1 is a schematic diagram for explaining an ultrasonic measurement apparatus 1000 according to the preferred embodiment of the present invention.

A reference numeral 1010 denotes a first ultrasonic probe, and 1020 a second ultrasonic probe. Each of the ultrasonic probes is constructed to include a plurality of vibrators. 1015 denotes an ultrasonic wave transmitting area of the first ultrasonic probe 1010, and 1011 denotes the direction of an acoustic axis of an ultrasonic wave of the first ultrasonic probe 1010. Also, 1025 denotes an ultrasonic wave transmitting area of the second ultrasonic probe 1020, and 1021 denotes the direction of an acoustic axis of an ultrasonic wave of the second ultrasonic probe 1020. In an example of FIG. 1, the first and second ultrasonic probes 1010, 1020 are arranged in such a manner that their acoustic axes cross each other and their ultrasonic wave transmitting areas 1015, 1025 overlap each other. The ultrasonic measurement apparatus 1000 can measure displacement related information on an object 1089 to be measured (e.g., tumors, lumps, internal organs, etc.) located in an overlapped portion between the ultrasonic wave transmitting areas 1015, 1025.

1040 denotes an information acquisition unit that acquires information on whether a current period is an increase period or a decrease period. The increase period means a period in which a temporal change of a force applied to the object 1089 to be measured or a temporal change of an amount of deformation of the object to be measured indicates a tendency of increase, and the decrease period means a period in which the temporal change of the force or the amount of deformation indicates a tendency of decrease.

Figure 2:
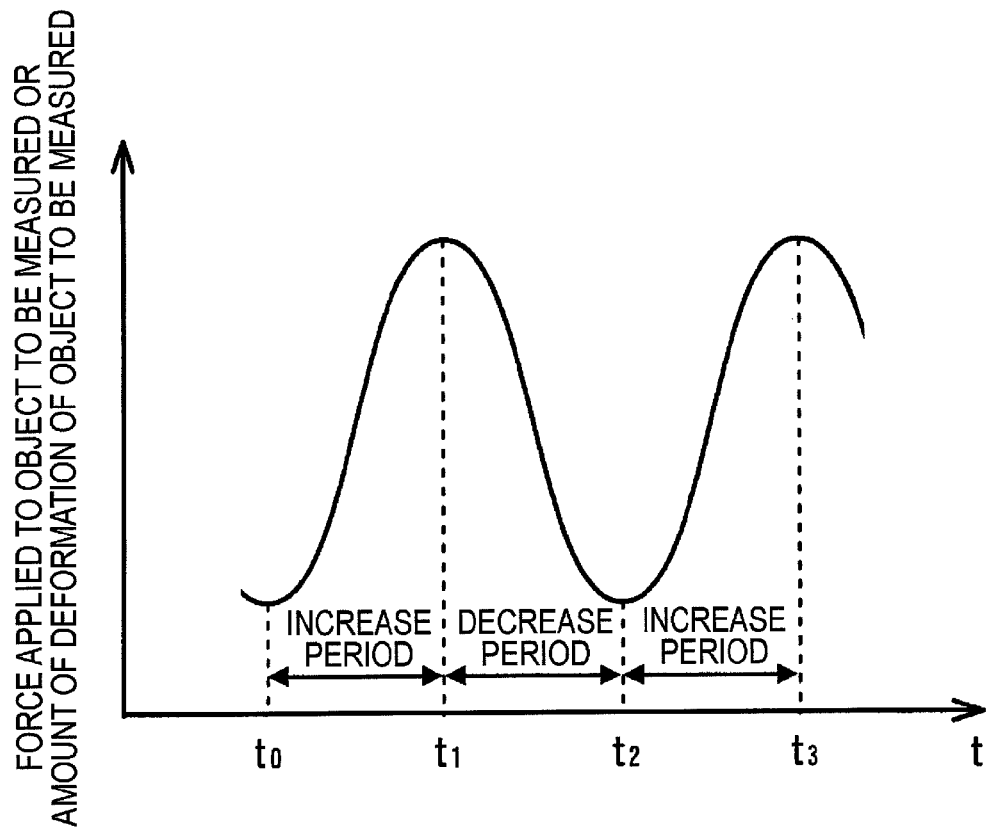
FIG. 2 is a view for explaining an increase period and a decrease period of a force applied to an object to be measured or of an amount of deformation of the object to be measured.

FIG. 2 illustrates one example of information (a signal) that is output by the information acquisition unit. In FIG. 2, the ordinate axis represents the force applied to the object to be measured or the amount of deformation of the object to be measured, and the abscissa represents time. Here, note that the amount of deformation of the object to be measured can be caught as an amount of displacement of a point (e.g., a center of gravity, an end point, etc.) or a boundary line, or it can be caught as an amount of change of the height or width of the object to be measured. In FIG. 2, a duration from t0 to t1 is an increase period, a duration from t1 to t2 is a decrease period, and a duration from t2 to t3 is an increase period. When displacement related information is measured, the object 1089 to be measured is caused to deform in a periodic manner by indirectly applying a periodic force to the object 1089 to be measured from outside a human body 1099 by means of an ultrasonic probe or a compressing device arranged separately therefrom. However, in a case where an object having a periodic motion or deformation even in the absence of an external pressure force, such as cardiac muscle movement of a heart, is measured, there is no need to apply a force thereto from outside.

1060 denotes a transmitting circuit that inputs signals for transmitting ultrasonic waves to the first and second ultrasonic probes 1010, 1020. 1090 denotes a receiving circuit that receives signals produced by the first and second ultrasonic probes 1010, 1020 upon reception of the ultrasonic waves. The receiving circuit 1090 amplifies reflection signals received by the ultrasonic probes, performs suitable delay amount control on the signals of the individual elements or probes, and performs phased addition thereof. 1050 denotes a processing unit for performing calculation processing to be described later. 1080 denotes an output unit, such as for example a display, for outputting the information obtained by the processing unit 1050. 1070 denotes a system control unit for controlling the transmitting circuit 1060, the receiving circuit 1090, the processing unit 1050, and the output unit 1080. The system control unit 1070 controls the transmitting and receiving timings and the transmitting and receiving frequencies of the transmitting circuit 1060 and the receiving circuit 1090, for example.

The first ultrasonic probe 1010 receives the ultrasonic wave reflected by the object 1089 to be measured which is located in the overlapped portion between the ultrasonic wave transmitting areas 1015, 1025, and produces first received data. In addition, the second ultrasonic probe 1020 receives an ultrasonic wave reflected by the object 1089 to be measured, and produces second received data. The first and second received data are respectively input to the processing unit 1050.

The processing unit 1050 calculates first displacement related information concerning a first direction of the object 1089 to be measured by using data in either one of an increase period and a decrease period, among the above-mentioned first received data. Further, the processing unit 1050 calculates second displacement related information concerning a second direction of the object 1089 to be measured by using data in the same period as that used to calculate the first displacement related information, among the second received data. For example, the processing unit 1050 first calculates the first displacement related information by using received data obtained in an increase period from t0 to t1 in FIG. 2, and then calculates the second displacement related information, too, from received data obtained in the increase period from t0 to t1. Specifically, a displacement can be obtained from received data that have been received at mutually different points in time within the range of from t0 to t1. Then, a strain can be obtained from the displacement as necessary, or if a force applied to the object to be measured is known, the elastic modulus of the object to be measured can be obtained. Here, the first direction is a traveling direction of the ultrasonic wave emitted from the first ultrasonic probe 1010, and typically coincides with the acoustic axis direction 1011 of the ultrasonic wave from the first ultrasonic probe. Also, the second direction is a traveling direction of the ultrasonic wave emitted from the second ultrasonic probe 1020, and typically coincides with the acoustic axis direction 1021 of the ultrasonic wave from the second ultrasonic probe. Here, note that the above-mentioned first and second displacement related information can be obtained in individual periods, respectively, which exhibit a common tendency. In other words, "the data in the same period as that used to calculate the first displacement related information" includes a case where the above-mentioned first displacement related information is obtained in a range from time point t0 to time point t1, and the above-mentioned second displacement related information is acquired by using data in a part of the period included from time point t0 to time point t1. In addition, a time point located on the boundary of an increase period and a decrease period is defined as included in both of these periods.

In addition, the output unit 1090 outputs the information of the object 1089 to be measured by using the above-mentioned first and second displacement related information. Specifically, the output unit 1090 can output the first and second displacement related information at the same time, but also can selectively output only one of the first and the second displacement related information. Further, the output unit 1090 can output multi-dimensional displacement related information that has been produced based on the first and second displacement related information. The displacement related information can be output in the form of numeric data, or can also be output in the form of image information. In addition, the output unit 1090 can provide a synthetic (overlapped) indication of the displacement related information, such as an ultrasonic tomographic image (B mode image, etc.) which is produced from the received data. For example, numeric data can be displayed at a pertinent position of the object 1089 to be measured in the ultrasonic tomographic image, or the ultrasonic tomography image can be displayed with the magnitude of the value of a displacement, strain, elastic modulus, or the like being represented by a pseudocolor. With such output results, the strain characteristic and the elastic property of the object 1089 to be measured (a tumor, etc.) lying in the interior of the human body 1099 can be inspected in an easy manner, and hence can be used for diagnosis.

When the transmitting and receiving of the first ultrasonic probe 1010 and the transmitting and receiving of the second ultrasonic probe 1020 are performed at different timings, first and second received data having been received at different time points cannot help being used. In such a case, in this embodiment, it is inhibited to use the received data obtained in an increase period and the received data obtained in a decrease period in combination or in a mixed manner. Displacement related information must necessarily be calculated from those pieces of received data which have been obtained in the same period (or in the same kind of periods). As a result, a displacement in each direction can be calculated from those pieces of received data in which the state of deformation and the behavior of the object 1089 to be measured are common, and hence it is possible to obtain strain information and elastic parameter information which have extremely high utility and high accuracy.

Here, note that in case where the first and second ultrasonic probes are fixed beforehand by means of unillustrated jigs, and the positional relation of both (i.e., the relative positions and directions of the probes) is known, strain information in specific two directions is obtained. Of course, even in a case where the ultrasonic probes are not fixed by jigs, if each of the ultrasonic probes is provided with a sensor for detecting and outputting information on the position and direction of a corresponding probe, it is possible to convert the information from each sensor into strain information in predetermined directions. Details will be described below.

Moreover, when only the data received in an increase period is used, the transmitting of an ultrasonic wave from each probe can be performed as follows. i) An ultrasonic signal is always sent and received regardless of an increase period or a decrease period, and the processing unit 1050 extracts only received data in an increase period as an object to be processed. ii) An ultrasonic signal is always sent regardless of an increase period or a decrease period. However, receiving is performed by both of the above-mentioned first and second ultrasonic probes only in an increase period(s). iii) The transmitting and receiving of ultrasonic signals by the first and second ultrasonic probes are performed only in an increase period(s). In a case where only the data received in a decrease period is used, the same discussion can also be applied. Of course, the present invention is not limited to the transmitting and receiving control of ultrasonic signals described in i), ii) and iii).

(First and Second Ultrasonic Probes)

In the present invention, two or more ultrasonic probes need only be provided, and a frequency band in the range of from 1 MHz to 15 MHz for example is used.

In the construction in which the ultrasonic probes are relatively fixed with respect to each other by means of jigs or the like, the relative positional relation information of the probes (i.e., information on the relative positions and directions of the probes) is known beforehand. However, from the point of view of ensuring a high degree of freedom for the arrangement of the probes, it is desirable that sensors be provided for the probes, respectively, so as to acquire the above-mentioned positional relation information by using information from the sensors. The sensors mentioned here include magnetic sensors, optical sensors, encoders, etc., which are able to acquire information on six axial directions. In particular, it is preferable that the accuracy of the sensors be 1 mm or less.

On the other hand, in case where the ultrasonic probes are not fixed to each other by means of jigs, it is a desirable form to confirm that the measurement areas (1015, 1025 in FIG. 1) or the directions of acoustic axes of both the ultrasonic probes cross each other by the use of the above-mentioned sensors.

In a case where a plurality of ultrasonic probes are fixed with respect to one another by means of jigs, it is preferable that the plurality of ultrasonic probes be respectively arranged in positions of n symmetries (n being an integer equal to two or more). This is because an asymmetrical arrangement of the ultrasonic probes induces asymmetry to the positional accuracy of the probes, and hence is disadvantageous in view of the theory of errors.

In addition, it is a desirable form to fix the relative positions of the plurality of ultrasonic probes in such a manner that the probes are arranged apart from one another by a distance of 10 mm or more (but equal to or less than 400 mm) This is because a problem of accuracy will arise if the relative positions are too close to one another, and the advantageous effect of using a plurality of probes is reduced.

By using these ultrasonic probes, it becomes possible to acquire the displacement information and strain information of the object to be measured with respect to the fixed directions. Here, note that if information on the pressure applied to the object to be measured is used, it is also possible to acquire information on the elastic modulus of the object to be measured from the displacement information and the pressure information.

In the ultrasonic measurement apparatus using the plurality of ultrasonic probes, it is possible to make the frequencies of the ultrasonic waves output from the individual probes different from one another so as to prevent interference or the like when the probes receive the ultrasonic waves. The reason for this is as follows. If it can be identified, from the received signals according to the frequency separation, which received signals have been produced by the ultrasonic waves output by which probes, incorrect signal processing can be avoided. Transmitting and receiving the ultrasonic waves at frequencies different from one another in this manner can be set beforehand. Alternatively, the system control unit 1070 can control the transmitting circuit 1060 and the receiving circuit 1090 in such a manner that the first and second ultrasonic probes can transmit and receive ultrasonic waves of different frequencies from each other.

In addition, it is considered that interference upon reception of the ultrasonic waves will be generated when there is an overlap between the ultrasonic wave transmitting areas of the individual probes. To avoid such interference, it is considered the transmitting and receiving of the ultrasonic waves by the ultrasonic probes are performed in an alternate manner, as shown in FIG. 10. On the other hand, in a case where tomographic images of the object to be measured are produced and displayed based on the received signals acquired by individual probes, if the transmitting and receiving of signals between the plurality of probes are performed alternately, as shown in FIG. 10, the frame rate has to be dropped, thus making it difficult to provide a smooth display of images. Therefore, when information on multi-dimensional strains is acquired by using the plurality of ultrasonic probes, i.e., when the transmitting and receiving of signals are performed with the measurement areas of the individual probes being overlapped with each other, it can also be constructed such that the transmitting and receiving of the signals are carried out between the probes in an alternate manner, as shown in FIG. 10. In addition, in a case where it is not necessary to acquire information on multi-dimensional strains, or in a case where there is no overlap between the ultrasonic wave transmitting areas of the individual probes, image information with a high frame rate can be acquired by just one probe so as to improve the frame rate. A specific flow is illustrated in FIG. 11. First of all, information on the relative positions and directions of the first and second ultrasonic probes is acquired (S1). Then, the transmitting areas of the first and second ultrasonic probes are input (S2), and it is determined whether the ultrasonic wave transmitting areas of the first and second ultrasonic probes overlap with each other (S3). When they overlap with each other (S3, "YES"), the two probes are used with their transmitting timings being shifted with respect to each other (S4). On the other hand, when they do not overlap with each other (S3, "NO"), the transmitting and receiving of ultrasonic waves are performed by using one of the two probes (S5). The transmitting timings of the ultrasonic waves by the individual probes can be controlled by means of the system control unit 1070.

The processing unit 1050 can produce multi-dimensional displacement related information from the above-mentioned first and second displacement related information based on a relative relation between the above-mentioned first direction and second direction, and can output the multi-dimensional displacement related information to the output unit 1080. In a case where the sensors are provided for acquiring information on the relative positions and directions of the first and second ultrasonic probes 1010, 1020 as previously stated, the processing unit 1050 can acquire the relative relation between the first direction and the second direction by using information acquired from the sensors. The processing unit 1050 can produce the multi-dimensional displacement related information by coordinate-transforming the first and second displacement related information from a coordinate system (oblique coordinate system) composed of the above-mentioned first and second directions into an orthogonal coordinate system. Here, it is preferable that the first and second ultrasonic probes be each provided with a sensor for outputting information on the position and direction of a corresponding probe, as in the examples to be described below.

It is also a preferable form to provide a device that outputs information (e.g., a screen display or a notification sound) on whether the ultrasonic wave transmitting area 1015 of the first ultrasonic probe 1010 and the ultrasonic wave transmitting area 1025 of the second ultrasonic probe 1020 have an overlapped portion is output. In addition, it is also a preferable form to provide a device that outputs information (e.g., a screen display or a notification sound) on whether the acoustic axis 1011 of the ultrasonic wave of the first ultrasonic probe 1010 and the acoustic axis 1021 of the ultrasonic wave of the second ultrasonic probe 1020 cross each other. By outputting such information, it becomes possible to inform an operator of whether the positions and directions of the probes are appropriate for measuring the multi-dimensional displacement related information, thus making it possible to improve operability and usability. Here, note that the processing unit 1050 can determine, based on information on the positions and directions of the probes, whether there is an overlap between the ultrasonic wave transmitting areas and whether the acoustic axes cross each other.

(Information Acquisition Unit)

The information acquisition unit 1040 can be composed of a pressure sensor, a velocity sensor, an acceleration sensor, a position sensor, or the like. By attaching a pressure sensor to a probe (or a compressing device), a force with which the probe or the like compresses the human body 1099 can be detected by means of the pressure sensor, so it becomes possible to indirectly detect the temporal change of a force applied to the object 1089 to be measured. Similarly, by attaching a velocity sensor, an acceleration sensor, a position sensor, or the like to a probe or a like element, it is possible to detect the displacement of the probe or the like element, so the temporal change of an amount of deformation of the object 1089 to be measured can be indirectly detected.

Here, note that the information acquisition unit can also calculate the temporal change of the amount of deformation of the object to be measured from the first received data or the second received data. That is, by analyzing received data at different time points, the amount of displacement (the amount of deformation) of the object to be measured can be acquired. Alternatively, image information (echo image) produced from received data can be analyzed. For example, by taking differences between time series images, the amount of displacement of the object to be measured (the amount of deformation) can be obtained. Thus, in a case where it is determined based on received data whether it is an increase period or a decrease period, the information acquisition unit is achieved as one function of the processing unit 1050.

(Compressing Device)

A compressing device for applying a force to the object 1089 to be measured can be provided separately from the first and second ultrasonic probes 1010, 1020. Of course, one or both of the first and second ultrasonic probes 1010, 1020 can be used as the compressing device.

In a case where the compressing device is provided separately from the above-mentioned ultrasonic probes, it can be arranged between the first and second ultrasonic probes 1010, 1020. When three or more ultrasonic probes are used, it is preferable to arrange the compressing device inside a polygon that is formed by the ultrasonic probes. Such an arrangement serves to make the measured amounts of displacement of the individual probes due to compression substantially equal to one another, thereby providing an effect of improving the accuracy of measurement.

In addition, in a case where the plurality of ultrasonic probes are relatively fixed with respect to one another by means of jigs, the above-mentioned compressing device can be arranged intermediate between the above-mentioned first and second ultrasonic probes, or at the center of, or at the center of gravity of, the polygon formed by the above-mentioned three or more ultrasonic probes. Of course, a plurality of compressing devices can be provided.

Hereinafter, reference will be made to specific examples of the present invention.

Example 1

Hereinafter, in a first example, reference will be made to a method of measuring the elastic property of a sample (an object to be measured) by compressing the sample.

Figure 3:
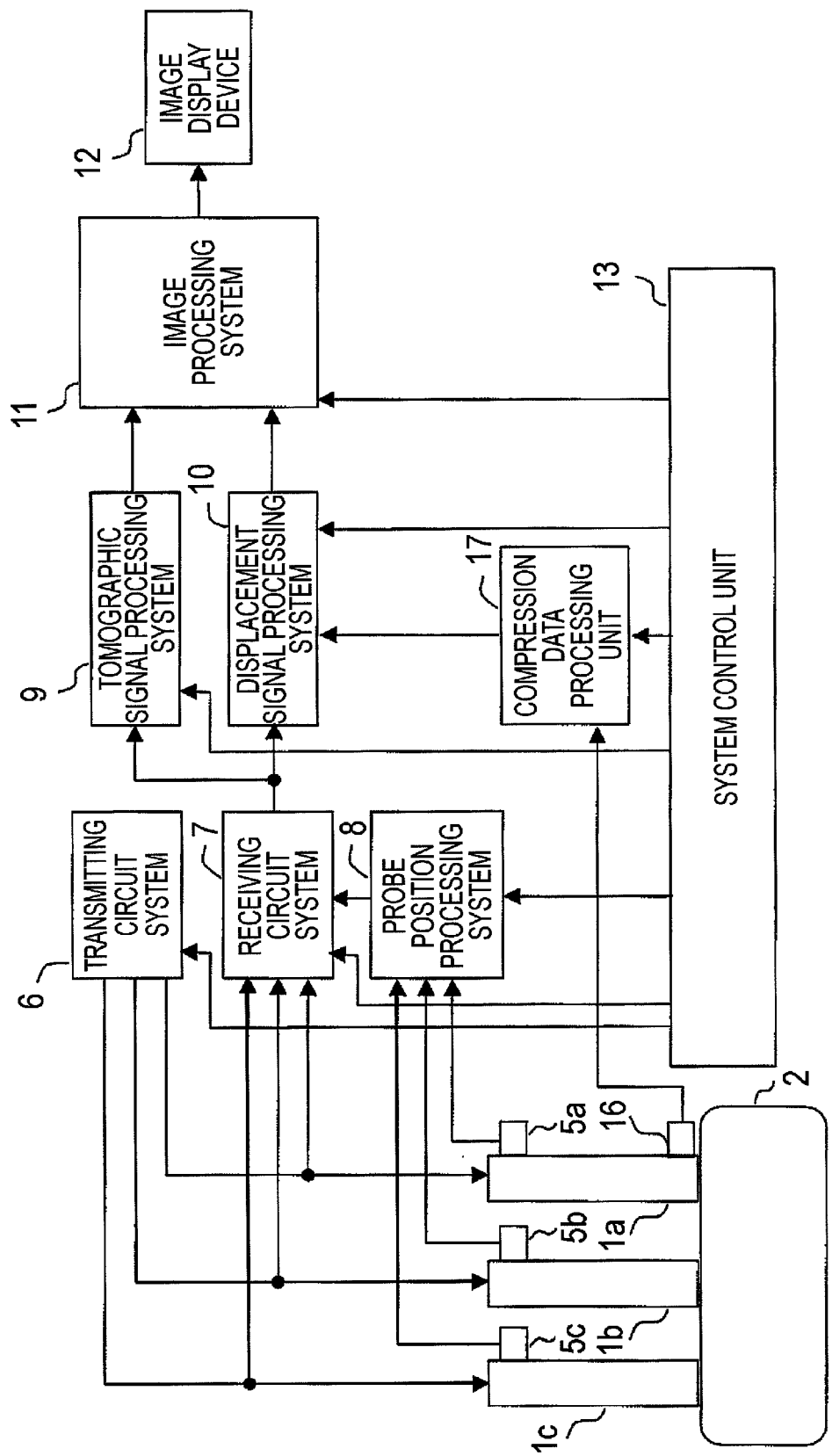
FIG. 3 is a view depicting the construction of an ultrasonic measurement apparatus commonly used in first through third examples of the present invention.

FIG. 3 is a schematic view of an ultrasonic measurement apparatus according to the first example. The flows of signals will be described below by using FIG. 3. The ultrasonic measurement apparatus is provided with a plurality of ultrasonic probes 1a, 1b, 1c, a transmitting circuit system 6, a receiving circuit system 7, a probe position processing system 8, a tomographic signal processing system 9, a displacement signal processing system 10, an image processing system 11, a image display device 12, a system control unit 13, and a compression data processing unit 17. Here, note that the displacement signal processing system 10 in FIG. 3 corresponds to the processing unit in the above-mentioned embodiment.

In FIG. 3, an ultrasonic wave transmitting instruction is forwarded to the transmitting circuit system 6 by the system control unit 13, and ultrasonic signals are sent from the transmitting circuit system 6 to the ultrasonic probes 1a, 1b, 1c. The ultrasonic probes 1a, 1b, 1c irradiate ultrasonic waves to the sample 2, and receive the ultrasonic waves reflected therefrom. In this case, the six-axis positions of the individual ultrasonic probes 1a, 1b, 1c are detected at any time by position sensors 5a, 5b, 5c, respectively, which are mounted on the individual ultrasonic probes 1a, 1b, 1c, respectively. The received ultrasonic signals and the received ultrasonic probe position signals are processed by the receiving circuit system 7 and the probe position processing system 8, respectively. In addition, the individual probe positions processed by the probe position processing system 8 are input to the receiving circuit system 7, so that they are used to correct the ultrasonic signals. Further, a pressure sensor 16 is mounted on the probe 1a, so that the state of a force applied to the probe 1a can be monitored. The pressure sensor 16 and the compression data processing unit 17 correspond to the information acquisition unit of the above-mentioned embodiment.

Then, the received signals are input to the tomographic signal processing system 9 and the displacement signal processing system 10, so that they are subjected to tomographic signal generation processing and displacement signal processing, respectively. The tomographic signal processing system 9 detects an envelop of the thus obtained ultrasonic signals, and inputs the strength thereof to the image processing system 11 as a luminance signal. The displacement signal processing system 10 processes the time variation of an ultrasonic signal corresponding to each point in the sample into a displacement signal, and inputs it to the image processing system 11 as a luminance signal or a color signal. These processing results are input to the image processing system 11 so that they are displayed as a tomographic signal and a displacement signal by means of the image display device 12.

Figure 4:
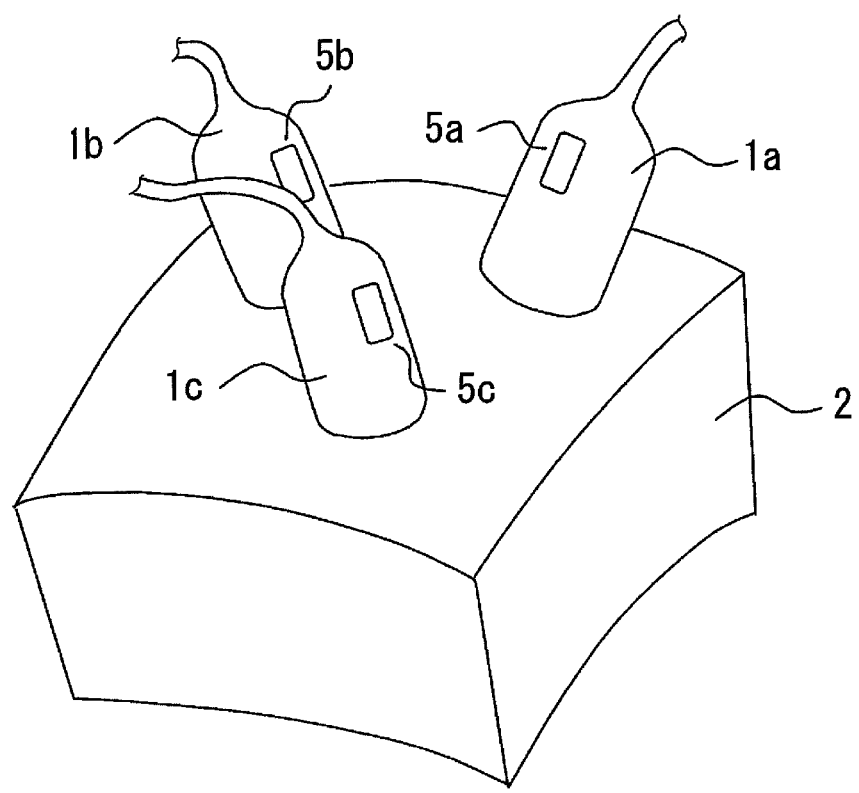
FIG. 4 is a view depicting the construction of probes in the first and second examples.

Next, reference will be made to the process of measuring the elastic property of the sample and the processing process of the displacement signal processing system 10. FIG. 4 is an enlarged view of probe portions of the ultrasonic measurement apparatus according to this example. The ultrasonic measurement apparatus of this example has three probes 1a, 1b, 1c, and irradiates ultrasonic waves from these probes to the sample 2. The measurement of the elastic property of the sample is achieved by generating strains in the sample. In this example, the sample is compressed by means of the probe 1a, and movements of individual points in the sample before and after the compression are then measured, whereby the displacement and strain of the sample are calculated. Further, by analyzing the pressure measured by the pressure sensor 16 by means of the compression data processing unit 17, it is determined whether the applied pressure is in an increasing tendency or in a decreasing tendency.

Amounts of strains in the individual points in the sample can be obtained by processing the reflected ultrasonic signals from the sample acquired by the three ultrasonic probes 1a, 1b, 1c. The concept of the signal processing is described below by using FIG. 5. FIG. 5 illustrates the movements of the sample before and after a compressing operation and individual ultrasonic signals obtained at those times. In a case where the sample contains a material as denoted at 2a having an acoustic impedance and an elastic parameter different from those of its surrounding, the signal obtained by the ultrasonic probe 1a accompanies strong reflection signal components on opposite side interfaces of the material, as denoted at 15a, 15b. When ultrasonic signals 15a, 15b are acquired before and after the sample is compressed, respectively, distances L, L' between the opposite side interfaces at those times can be measured. Accordingly, an amount of strain obtained by the ultrasonic probe 1a can be calculated as (L−L'). Similarly, with respect to the probes 1b, 1c, strains in the directions of individual axes thereof can be obtained by similar calculations.

In the actual signal processing, an amount of strain is calculated by the phase change of a signal or processing of obtained images, but in this example, the following description will be given by using a method called an autocorrelation method as a signal processing method. However, even if using a spatial correlation method or other appropriate calculation processing, it is possible to obtain substantially similar results. The autocorrelation method is to measure a phase difference of an ultrasonic signal at two different time, and is based on the principle described below, according to Japanese Patent Application Laid-Open No. H5-161647.

A received ultrasonic signal $S_1(t)$ reflected from a scatterer or scatting medium is denoted by the following Equation (1):

$$S_1(t) = A_1(t) \times \exp[-j(\omega_0 t + \Phi_1(t))] \qquad (1)$$

where $A_1(t)$ denotes amplitude, $\Phi_1(t)$ denotes phase, and $\omega_0$ denotes angular frequency of a transmitting signal.

Assuming that the received signal at the time when the scattering medium as a whole is displaced by $\Delta x$ is $S_2(t)$, this is represented by the following Equation (2):

$$\begin{aligned} S_2(t) &= S_1(t - \Delta t) \\ &= A_1(t - \Delta t) \times \exp[-j(\omega_0(t - \Delta t) + \Phi_1(t - \Delta t))] \end{aligned} \qquad (2)$$

Here, $\Delta t$ is a propagation time difference (displacement time) at the time when the scattering medium is displaced by $\Delta x$, and is denoted by the following Equation (3):

$$\Delta t = 2 \cdot \Delta x / c \qquad (3)$$

where c is the speed of sound.

Assuming that the outputs obtained by orthogonally detecting these received signals $S_1(t)$, $S_2(t)$ at an angular frequency of $\omega_0$ are denoted by $I_1(t)$, $Q_1(t)$, $I_2(t)$, $Q_2(t)$, respectively, phases $\theta_1(t)$, $\theta_2(t)$ are provided by the following Equations (4) and (5), respectively:

$$\begin{aligned} \theta_1(t) &= \Phi_1(t) \\ &= \tan^{-1}(Q_1(t)/I_1(t)) \end{aligned} \qquad (4)$$

$$\begin{aligned} \theta_2(t) &= \Phi_1(t - \Delta t) + \omega_0 \Delta t \\ &= \tan^{-1}(Q_2(t)/I_2(t)) \end{aligned} \qquad (5)$$

Accordingly, a phase difference $\Delta\theta$ between the phases $\theta_1(t)$, $\theta_2(t)$ before and after the displacement is provided by the following Equation (6):

$$\begin{aligned} \Delta\theta &= \theta_2(t) - \theta_1(t) \\ &= \Phi_1(t - \Delta t) - \Phi_1(t) + \omega_0 \Delta t \\ &= \tan^{-1}(Q_1(t)/I_1(t)) - \tan^{-1}(Q_2(t)/I_2(t)) \end{aligned} \qquad (6)$$

Here, because $\Phi_1(t-\Delta t)$ is substantially equal to $\Phi_1(t)$, Equation (6) above can be transformed into the following Equation (7):

$$\begin{aligned} \Delta x &= (c/2\omega_0)\Delta\theta \\ &= (c/2\omega_0)\{\tan^{-1}(Q_1(t)/I_1(t)) - \tan^{-1}(Q_2(t)/I_2(t))\} \end{aligned} \qquad (7)$$

Accordingly, the amount of displacement $\Delta x$ can be easily obtained by processing the ultrasonic signal with the use of Equation (7) above.

Figure 6:
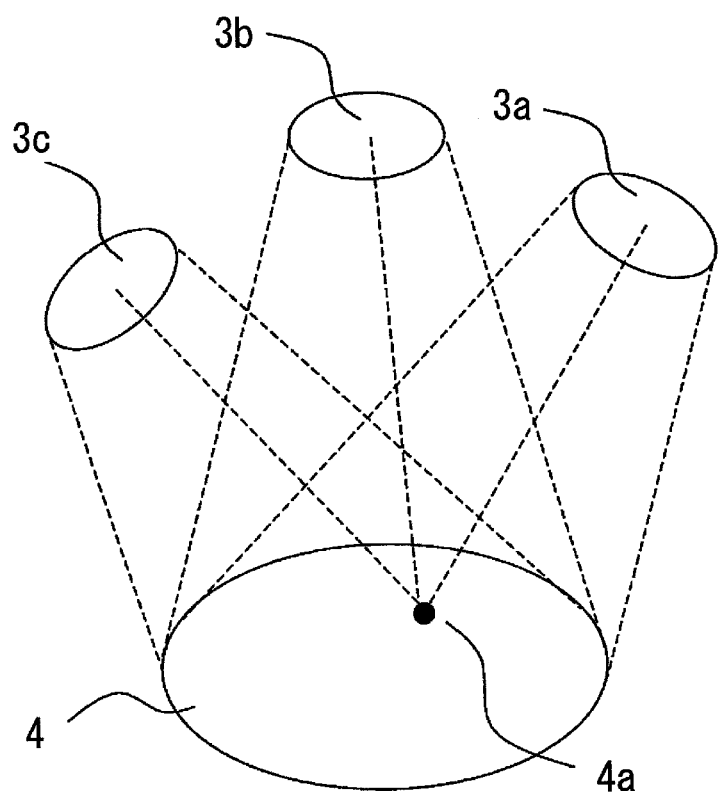
FIG. 6 is a view representing the relation among probe surfaces, fields of view, and a point of measurement.

Next, reference will be made to a method of obtaining the amounts of strains at individual points in the sample from the movements thereof. The movements of individual points in the sample due to the compression thereof are measured by means of the three ultrasonic probes $1a$, $1b$, $1c$. FIG. 6 diagrammatically illustrates the surfaces of the ultrasonic probes in FIG. 4, the fields of view of the individual probes, and a certain measurement point. The individual probe surfaces of the ultrasonic probes $1a$, $1b$, $1c$ are denoted by $3a$, $3b$, $3c$, and the one measurement point is denoted by $4a$. A coordinate system formed by acoustic axes directed from the individual ultrasonic probe surfaces to the one point in the sample is an oblique coordinate system, and a three-dimensional like movement of the point measured by the individual probes is recorded as a projection onto the oblique coordinate system by using the calculations of the above-mentioned Equations (1) through (7). Here, note that the relative positions of the individual probes are measured at any time by the six-axis sensors $5a$, $5b$, $5c$, so it is possible to convert the three-dimensional like movement thus recorded on the oblique coordinate system into a corresponding one on the orthogonal coordinate system by coordinate transformation. In addition, considering the ease of conversion and the ease of operation (usability), it is desirable that one axis of the oblique coordinate system and the orthogonal coordinate system coincide with the compression direction of the compressing device or the central axis of either one of the probes.

Accordingly, according to this example, the movement of each point in the sample can be measured in a three-dimensional manner, and accordingly, the amount of strain S can be obtained by the following Equation (8):

$$S = \begin{bmatrix} \partial/\partial x & 0 & 0 \\ 0 & \partial/\partial y & 0 \\ 0 & 0 & \partial/\partial z \\ 0 & \partial/\partial z & \partial/\partial y \\ \partial/\partial z & 0 & \partial/\partial x \\ \partial/\partial y & \partial/\partial x & 0 \end{bmatrix} \begin{bmatrix} u_x \\ u_y \\ u_z \end{bmatrix} \qquad (8)$$

where $u_x$, $u_y$, $u_z$ denote the amounts of displacement of each point in the sample. In other words, by performing the processing of Equation (8) above in a necessary region of the sample, it becomes possible to know the strain amount distribution in that region in an exact manner.

The elastic modulus distribution of the sample can be obtained from the strain distribution and the stress distribution in the interior of the sample, as shown in the following Equation (9):

$$T = C : S \qquad (9)$$

However, it is difficult directly to measure the stress distribution T in the interior of the sample under the present situation, so the elastic modulus distribution is calculated from a boundary condition for the strain distribution and the compression of the sample in a reverse engineering way. In addition, certain methods for calculating the elastic modulus distribution by making some assumptions have been attempted. In the following, one example of a technique for obtaining the elastic modulus distribution is shown.

In a case where an infinite uniform stress field of an infinite homogeneous medium is assumed upon calculation of the stress distribution, the following Equation (10) holds:

$$\begin{bmatrix} T_1 \\ 0 \\ 0 \\ 0 \\ 0 \\ 0 \end{bmatrix} = C:S \quad (10)$$

T1 can be measured by adding a pressure sensor to each ultrasonic probe. Accordingly, elastic modulus C can also be obtained. In addition, even if the stress field has a finite length, the stress distribution equation can be theoretically calculated in case of a homogeneous medium. That is, if T2–T6 are set equal to 0 in Equation (10) above, C:S becomes a function of T1, and hence it is possible to calculate the stress field.

Because the elastic modulus C can be obtained according to the above-mentioned calculations, it becomes possible to derive elastic parameters such as Young's modulus E, Poisson's ratio σ, etc., by using the following Equations (11) and (12):

$$E = C_{11} - \frac{2C_{12}^2}{C_{11} + C_{12}} \quad (11)$$

$$\sigma = \frac{C_{12}}{C_{11} + C_{12}} \quad (12)$$

Besides the above-mentioned methods, there have been proposed, as a method for deriving the elastic modulus from the strain, a method in which the sample is assumed to be non-compressive, a method using a finite element scheme, etc., and the elastic parameters can be derived according to similar calculations even with the use of any of such methods.

Next, detailed reference will be made to the acquisition timing of the ultrasonic signal. Ultrasonic data are acquired during compressing operations. The ultrasonic data that can be acquired include three kinds of data for the probes $1a$, $1b$, $1c$, and time series data before and after compression. In this example, the acquisition of data is performed in either of a pressure increase period and a pressure decrease period. FIG. 9 illustrates this state. In FIG. 9, the abscissa denotes time, and the ordinate denotes the compression pressure. As shown in this figure, individual pieces of ultrasonic data of the probes $1a$, $1b$, $1c$ are acquired in succession in an alternating manner (that is, one probe after another).

In the principle of this method, in data before and after a time point at which the direction of compression is reversed (i.e., a time point at which an increase period and a decrease period are changed over with each other), there is a very small difference in the amount of strain, so it is impossible to obtain significant data. Therefore, a determination as to the direction of compression is made by means of the compression data processing unit 17, so that when the direction of compression is reversed, data acquisition is not carried out. As a result, it becomes possible always to perform good strain amount measurements.

As described above, according to this example, it becomes possible to derive the displacement, strain, and elastic parameter of the sample from the ultrasonic signal.

In a case where the strain and elastic distributions are obtained by using the above-mentioned method, attention should be paid to the fact that the accuracy obtained differs according to the arrangement of the individual ultrasonic probes. This is because, as described above, the coordinate system in which the acoustic axes of the individual ultrasonic probes are formed is an oblique coordinate system, and hence, when the intervals between the adjacent ultrasonic probes are narrow, large errors are induced. When considering that the ultrasonic measurement apparatus of the present invention is used for medical diagnosis (i.e., used as a medical ultrasonic diagnostic apparatus), the sample is a human body, and the depth of observation is in the range of from several mm to several cm, so on the assumption that a maximum depth is 20 cm and the deterioration of accuracy is equal to or less than 5% of the orthogonal coordinate system, it is preferable that the probe interval (i.e., the interval between adjacent probes) be about 10 mm or more. In addition, it is necessary that the accuracy required of the sensors $5a$, $5b$, $5c$ is likewise less than the accuracy of measurement in the point of measurement. It is desirable that the sensor accuracy be 1 mm or less because the resolution of the medical ultrasonic diagnostic apparatus is 1 mm or less. Further, in order to minimize the measurement error of each ultrasonic probe, it is preferable that the ultrasonic probes have three symmetries.

Although the compressing device is one probe in the method of obtaining the strain and elastic distributions according to the above-mentioned schemes, two or three probes can be compressed simultaneously or alternately, whereby an overall amount of strain can be estimated by calculation from the respective amounts of strains obtained by compression of the individual probes. In this case, it is possible to output an appropriate calculation result, as required or corresponding to the object to be measured, such as an average value, a maximum value, a minimum value, a median value, etc.

Moreover, in this example, the pressure sensor is used for the purpose of making a determination as to an increase period or a decrease period. However, without the use of such a pressure sensor, similar effects can be achieved by calculating the direction of compression by using other sensor(s) such as a velocity sensor, an acceleration sensor, a position sensor, etc., or by analyzing the ultrasonic signals of the probes $1a$, $1b$, $1c$, or by analyzing a display output, or by like other methods. Alternatively, it is also possible to make a determination as to an increase period or a decrease period by analyzing the outputs of the position sensors $5a$, $5b$, $5c$ which are arranged for the purpose of measuring the positions and directions between the probes.

In this example, reference has been made to the case in which the number of ultrasonic probes employed is three, but even in a case where four or more plural probes are used, similar effects can be obtained by similar analogous calculation. Also, in the case of using two probes, similar effects can be achieved, though with reduced accuracy, by introducing an assumption of isotropy, etc. In addition, in a case where respective accuracies and symmetries are out of the ranges of this example, similar effects can still be achieved although accuracy is reduced.

Example 2

In a second example, reference will be made to a technique of measuring a strain of a sample according to a method which is different from the first example. In the first example, the strain of the sample is measured by compressing the sample, but in a case where a sample moves on its own, points of measurement in the sample also move, so the measurement of a strain in the sample can be carried out without performing a compressing operation. For example, a heart and its surrounding portions are caused to deform in a periodic manner in accordance with the movement of cardiac muscle, so a compressing operation from the outside is unnecessary. In such a case, the measurement of a strain in the heart or its surrounding portions is performed without moving the ultrasonic probes 1a, 1b, 1c in FIG. 3. In addition, the methods of measurement and calculation are quite the same as the first example, and similar effects can be achieved.

Example 3

Figure 7:
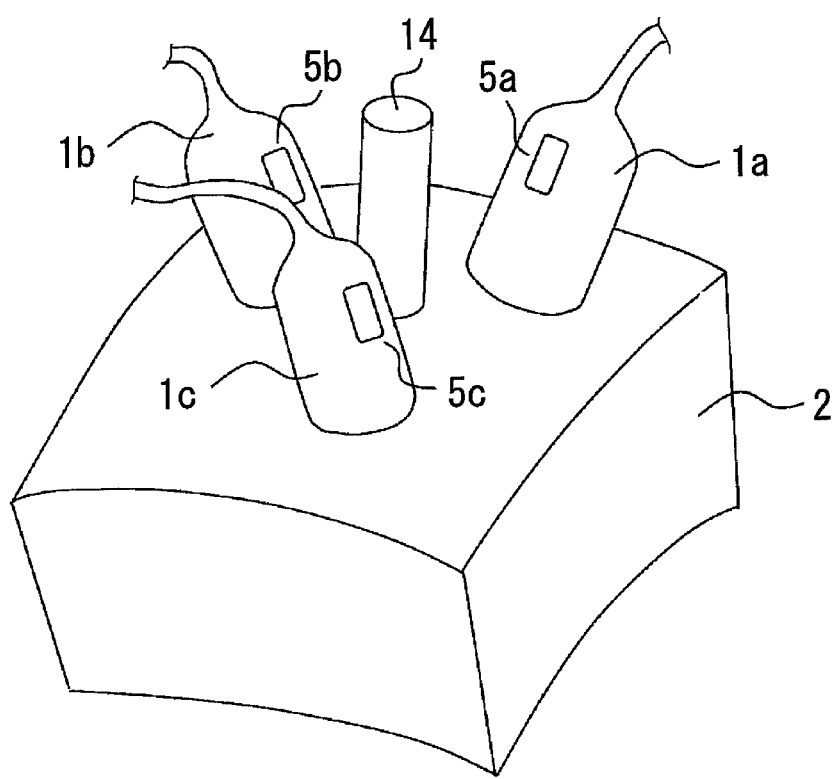
FIG. 7 is a view depicting the construction of probes and a compressing device in the third example.
Figure 8:
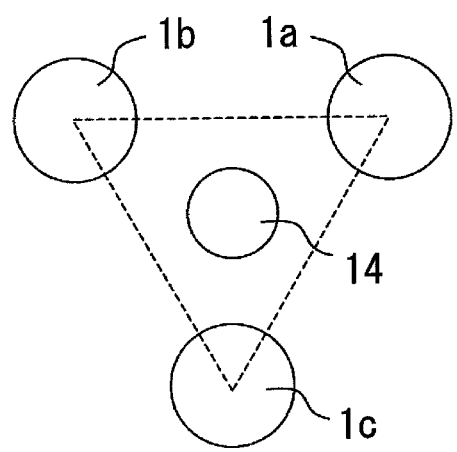
FIG. 8 is a view depicting the arrangement of the probes and the compressing device in the third example.

In a third example of the present invention, reference will be made to an example in which the measurement of an elastic modulus distribution is performed by using a compressing device which is different from the one used in the first example. FIG. 7 is a view illustrating a sample and its surroundings using this third example. Ultrasonic probes 1a, 1b, 1c, position sensors 5a, 5b, 5c, and a sample 2 are arranged similar to the first example, but in this third example, a compressing device 14 is provided in addition to the probes. The entire system of an ultrasonic measurement apparatus of this third example is similar to that of the first example (FIG. 3). At the time of measurement, the sample is compressed by the compressing device 14, and ultrasonic signals before and after the compression are acquired by the ultrasonic probes 1a, 1b, 1c. In addition, arranging the individual ultrasonic probes 1a, 1b, 1c and the compressing device 14 so as to have symmetry with one another provides the highest accuracy of measurement. Therefore, it is preferred that the ultrasonic probes 1a, 1b, 1c be arranged around the compressing device 14, which acts as an axis of symmetry, so as to have three symmetries, as shown in a top plan view of FIG. 8. According to this example, too, it is possible to acquire amounts of strains and elastic quantities similar to the first example.

Further, in order to perform measurements with sufficiently high accuracy, the probe interval is required to be about 10 mm or more, and the accuracy of each sensor is required to be 1 mm or less.

Although the number of compressing device used is one in the method of obtaining the strain and elastic distribution according to the above-mentioned scheme, two or three or more compressing devices or probes can be compressed simultaneously or alternately, whereby an overall amount of strain can be estimated by calculation from the respective amounts of strains obtained by compression of the compressing devices or the probes, respectively. In this case, it is possible to output an appropriate calculation result, as required or corresponding to the object to be measured, such as an average value, a maximum value, a minimum value, a median value, etc.

In this third example, reference has been made to the case in which the number of ultrasonic probes employed is three, but even in case where two, four or more plural probes are used, similar effects can be obtained by similar analogous calculation. In addition, in case where respective accuracies and symmetries are out of the ranges of this third example, similar effects can still be achieved though accuracy is reduced.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An ultrasonic measurement apparatus comprising:
a plurality of ultrasonic probes that includes, at least, a first ultrasonic probe and a second ultrasonic probe;
an information acquisition unit that acquires information on whether an increase period or a decrease period is in progress, the increase period being a period in which a temporal change of a force applied to an object to be measured or an amount of deformation of the object to be measured exhibits a tendency of increase, and the decrease period being a period in which the temporal change of the force or the amount of deformation exhibits a tendency of decrease, wherein the object to be measured exhibits periodic motion or deformation;
a transmitting circuit that inputs signals for transmitting ultrasonic waves to said first and second ultrasonic probes, inputting such signal for transmitting ultrasonic waves to said first ultrasonic probe only when not inputting such signal for transmitting ultrasonic waves to said second ultrasonic probe, and vice versa;
a receiving circuit that receives signals produced by said first and second ultrasonic probes upon reception of ultrasonic waves;
a processing unit;
an output unit; and
a system control unit that controls said transmitting circuit, said receiving circuit, said processing unit, and said output unit,
wherein said first ultrasonic probe is positioned such that it receives an ultrasonic wave reflected by the object to be measured which is located in an overlapped portion between an ultrasonic wave transmitting area of said first ultrasonic probe and an ultrasonic wave transmitting area of said second ultrasonic probe, and produces first received data, and
said second ultrasonic probe is positioned such that it receives an ultrasonic wave reflected by the object to be measured which is located in the overlapped portion, and produces second received data, said system control unit controlling, based at least in part on the information acquired by said information acquisition unit, such that said second ultrasonic probe receives the ultrasonic wave and produces the second received data at a time different from the time at which said first ultrasonic probe is producing the first received data, and
wherein said processing unit, based in part on the information acquired by said information acquisition unit,
calculates first displacement-related information concerning a first direction of the object to be measured by using data in only either one period of the increase period or the decrease period among the first received data, such that all the first displacement-related information is calculated using only data from that one increase period or decrease period, and
calculates second displacement-related information concerning a second direction of the object to be measured by using data in only the same period as that used to calculate the first displacement related-information among the second received data, and
wherein said output unit outputs information on the object to be measured by using the first and second displacement-related information, and
wherein said system control unit controls said transmitting circuit and said receiving circuit so that transmission and receiving of ultrasonic waves by said first ultrasonic probe is not performed at the same time as, but alternates with, transmission and receiving of ultrasonic waves by said second ultrasonic probe.

2. The ultrasonic measurement apparatus according to claim 1, wherein said information acquisition unit detects the temporal change of the force applied to the object to be measured or of the amount of deformation of the object to be measured by means of a pressure sensor, a velocity sensor, an acceleration sensor, or a position sensor.

3. The ultrasonic measurement apparatus according to claim 1, wherein said information acquisition unit calculates the temporal change of the amount of deformation of the object to be measured from the first received data or the second received data.

4. The ultrasonic measurement apparatus according to claim 1, further comprising:
 a compressing device that applies a force to the object to be measured.

5. The ultrasonic measurement apparatus according to claim 4, wherein said compressing device is located between said first and second ultrasonic probes or inside a polygon that is formed by said plurality of ultrasonic probes.

6. The ultrasonic measurement apparatus according to claim 5, further comprising a jib, wherein said plurality of ultrasonic probes are fixed relative to one another by means of said jig, and said compressing device is located intermediate between said first and second ultrasonic probes, or in the center, or the center of gravity, of said polygon.

7. The ultrasonic measurement apparatus according to claim 1, wherein the displacement-information is information on a displacement, a strain or an elastic modulus of the object to be measured.

8. The ultrasonic measurement apparatus according to claim 1, further comprising:
 a unit that outputs information on whether the ultrasonic wave transmitting area of said first ultrasonic probe and the ultrasonic wave transmitting area of said second ultrasonic probe have the overlapped portion.

9. The ultrasonic measurement apparatus according to claim 1, further comprising:
 a unit that outputs information on whether an acoustic axis of an ultrasonic wave of said first ultrasonic probe and an acoustic axis of an ultrasonic wave of said second ultrasonic probe cross each other.

10. The ultrasonic measurement apparatus according to claim 1, wherein said system control unit controls said transmitting circuit and said receiving circuit so that said first and second ultrasonic probes transmit and receive ultrasonic waves of different frequencies from each other.

11. The ultrasonic measurement apparatus according to claim 1, wherein said processing unit produces multi-dimensional displacement-related information from said first and second displacement-related information based on a relative relation between the first direction and the second direction, and outputs the multi-dimensional displacement-related information to said output unit.

12. The ultrasonic measurement apparatus according to claim 11, further comprising:
 a sensor that acquires information on the relative positions and directions of said first and second ultrasonic probes, wherein said processing unit acquires the relation between the first direction and the second direction by using information acquired from said sensor.

13. The ultrasonic measurement apparatus according to claim 11, wherein said processing unit produces the multi-dimensional displacement related information by coordinate transforming the first and second displacement-related information from a coordinate system composed of the first and second directions into an orthogonal coordinate system.

* * * * *